US005577026A

United States Patent [19]
Gordon et al.

[11] Patent Number: 5,577,026
[45] Date of Patent: Nov. 19, 1996

[54] APPARATUS FOR TRANSFERRING DATA TO AND FROM A MOVING DEVICE

[75] Inventors: Bernard M. Gordon, Magnolia; Richard B. Johnson, Beverly; Iosef Izrailit, Newton; Hans Weedon, Salem, all of Mass.; Douglas Abraham, New Market, N.H.

[73] Assignee: Analogic Corporation, Peabody, Mass.

[21] Appl. No.: 174,664

[22] Filed: Dec. 28, 1993

[51] Int. Cl.⁶ .................................................. H04B 1/56
[52] U.S. Cl. .............................. 370/24; 455/41; 382/131; 382/132; 343/841
[58] Field of Search ............................. 370/85.3, 29, 30, 370/69.1, 6, 24, 38, 50; 343/700 MS, 841, 705, 895, 897; 375/303; 455/279, 129, 41, 269; 378/198, 20, 11; 250/363.05; 382/131, 132, 128

[56] References Cited

U.S. PATENT DOCUMENTS

| | | | |
|---|---|---|---|
| 2,573,914 | 11/1951 | Landon | 343/841 |
| 4,101,833 | 7/1978 | Bingham et al. | 370/30 |
| 4,538,125 | 8/1985 | Beckmann et al. | 333/248 |
| 4,555,631 | 11/1985 | Martens | 250/551 |
| 4,596,022 | 6/1986 | Stoner | 375/272 |
| 4,796,183 | 1/1989 | Ermert et al. | 364/413.15 |
| 5,132,966 | 7/1992 | Hayano et al. | 370/94.1 |
| 5,134,422 | 7/1992 | Auriol | 343/895 |
| 5,140,696 | 8/1992 | Fox | 455/41 |
| 5,351,249 | 9/1994 | Lomp et al. | 375/303 |

FOREIGN PATENT DOCUMENTS

8429531 U   5/1986   Germany .

OTHER PUBLICATIONS

Computer Applications, vol. II of Queueing Systems, 1976 by John Wiley & Sons, Inc., New York, pp. 26–5 and 32–15.

Primary Examiner—Douglas W. Olms
Assistant Examiner—Ajit Patel
Attorney, Agent, or Firm—Lappin & Kusmer LLP

[57] ABSTRACT

An apparatus is provided for transferring data between a first device and a second device, the second device being adapted to rotate with respect to the first device. The first device includes a first antenna assembly and a first transceiver assembly for transmitting and receiving signals via the first antenna assembly. The second device includes a second antenna assembly and a second transceiver assembly for transmitting and receiving signals via the second antenna assembly. The rotating antenna assembly is mounted circumferentially about the second device such that the stationary antenna is in capacitive coupling relationship substantially through an entire revolution of the second device. The apparatus is particularly useful in a CT scanner where data is transmitted from the first device to the second device via a single channel, and data is transmitted from the second device to the first device via two time-multiplexed channels so as to provide high speed data transfer from the second device to the first device at twice the rate of data transfer from the first device to the second device. The invention includes a variety of features for significantly reducing error rates, and particularly for reducing errors due to cross talk between channels.

75 Claims, 7 Drawing Sheets

APPARATUS FOR TRANSFERRING DATA TO AND FROM A MOVING DEVICE

FIELD OF THE INVENTION

This invention relates generally to data communications, and more particularly to apparatus for transferring data to and from a rotating device.

BACKGROUND OF THE INVENTION

It is well known to use electro-mechanical slip rings, to enable the transfer of data to and from a rotating device, such as the drum that is rotatably mounted in the gantry of a computer tomography (CT) scanner so that the X-ray equipment supported by the drum can be rotated about a patient during a tomographic scan. However, over long periods of use, mechanical wear and contamination can occur, leading to reduced electro-mechanical contact reliability, possibly resulting in loss of data. Further, where the rotating device is relatively large, such as the drum of a CT scanner, the use of commensurately large slip rings adds significant weight to the total weight of the CT scanner.

In addition, where the rotating device, such as a rotatable drum of a CT scanner, rotates a limited amount with each use, it is also known to transfer data to and from the drum through cables, which are wound and unwound as the device alternately rotates clockwise and counterclockwise. Again, disadvantages include additional weight due to the use of cables, the effects of the attached cables on the rotation of the rotating device, and decreased reliability due to, for example, the vulnerability of cables to disconnection and breakage when the cables are repeatedly wound or overwound.

U.S. Pat. Nos. 4,928,283 and RE 34,379 briefly describe a CT scan system employing a "two-way communication link" between "an electronics package" secured to the disk of the machine and a "computer used for image processing and control". No further detail is provided.

OBJECTS OF THE INVENTION

It is a general object of the present invention to provide an apparatus for transferring data to and from a moving device that significantly overcomes the problems of the prior art.

A more specific object of the present invention is to provide an apparatus for transferring data to and from a rotating device through a medium which is not required to be mechanically connected to the device as it rotates about its axis.

A further object of the present invention is to allow a rotating device to rotate for an extended period of time, allowing data to be transferred to and from the device at any time during the extended period.

Another object of the invention is to provide an apparatus for reliably transferring data to and from a rotating device without the use of cables or slip rings.

And another object of the invention is to provide a light weight apparatus for reliably transferring data to and from a rotating device, and particularly useful in CT scanners so as add little weight to the scanner.

Yet another object of the invention is to provide apparatus, particularly useful in CT scanners, for reliably transferring data to and from a rotating device with relatively low power consumption.

Still another object of the invention is to provide an apparatus for transferring data to and from a rotating device and particularly useful in CT scanners, while being significantly unaffected by electromagnetic interference.

And yet another object of the invention is to provide an apparatus for transferring data to and from a rotating device at relatively high data transfer rates, and being particularly useful in CT scanners.

And still another object of the invention is to provide an apparatus for transferring data to and from a rotating device at relatively low data error rates, and being particularly useful in CT scanners.

Other objects of the present invention will in part be suggested and will in part appear hereinafter. The invention accordingly includes the apparatus possessing the construction, combination of elements, and arrangement of parts, all of which are exemplified in the following detailed disclosure and the scope of the application, all of which will be indicated in the claims.

SUMMARY OF THE INVENTION

An apparatus is provided for transferring data between a first device and a second device that rotates with respect to the first device. The first device preferably is stationary and includes a fixed, stationary antenna assembly and a fixed transceiver for transmitting and receiving signals within a preselected part of the electromagnetic spectrum via the stationary antenna assembly as the second device rotates relative thereto. The rotating device preferably includes a rotating antenna assembly and a rotating transceiver for transmitting and receiving the signals via the rotating antenna assembly to and from the stationary antenna assembly. The rotating antenna assembly is mounted circumferentially about the rotating device such that the stationary antenna assembly is capacitively coupled to the rotating antenna assembly regardless of the instantaneous angular position of the rotating device.

In the preferred apparatus of the invention, data is transferred from the stationary device to the rotating device by encoding and modulating the data within the stationary transceiver, and then transmitting the encoded and modulated data within the preselected part of the electromagnetic spectrum from the stationary antenna assembly to the rotating antenna assembly via an air gap therebetween. The rotating transceiver receives the encoded and modulated data, and then at least demodulates and decodes it to extract the original data. Data is communicated from the rotating device to the stationary device in the same manner.

In a preferred embodiment, where more data is transmitted from the rotating device to the stationary device, data is transmitted from the stationary device to the rotating device via a single channel, and data is transmitted from the rotating device to the stationary device via two time-multiplexed channels so as to provide high speed data transfer from the rotating device to the stationary device.

The invention includes a variety of features for significantly reducing error rates, and particularly for reducing errors due to cross talk between channels. For example, the data can be transferred at a signal-to-noise ratio of less than about 20 dB. The invention provides data error rates which are significantly better, such as about one error in five trillion bits. In a preferred embodiment, to reduce cross talk, data is transferred using frequency shift keying (FSK), wherein the frequencies employed for modulating data transferred from the stationary device to the rotating device are different from the frequencies used for modulating data transmitted from the rotating device to the stationary device. Channel separation is further improved by spatially separating the antennas of the two channels used for "down link" transmission from the rotating device to the stationary device. Also, grounded conductors separate the down link from the "up link" channels. To reduce errors due to geometric and mechanical imperfections of the rotating device relative to the stationary device, the antenna assembly on the rotating device is adapted to remain in capacitive coupling relationship with the antenna assembly on the stationary device throughout each complete revolution of the rotating device. Thus, data can be reliably sent and received at a relatively fast data rate, e.g., approximately 10 megabits per second, over each channel substantially independent of the position of the rotating device.

The invention is useful whenever information must be transferred between a rotating system and a stationary system, such as a CT scanner, where control and information data can advantageously be transferred in real time.

BRIEF DESCRIPTION OF THE DRAWINGS

The invention will be more fully understood from the following detailed description, in conjunction with the accompanying figures, wherein.

DETAILED DESCRIPTION OF THE DRAWINGS

Figure 1:
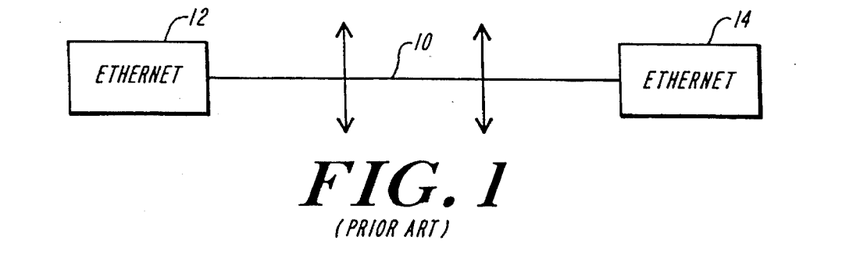
FIG. 1 is a block diagram of a prior art ETHERNET communications network.

With reference to FIG. 1, it is known to transmit serial data at high speed over coaxial cable 10 using various protocols and encoding techniques. Each node at which data is transmitted and/or received on the cable is provided with a transceiver, such as indicated at 12 and 14. One commonly used protocol is ETHERNET. An ETHERNET transceiver preferably uses standard encoding techniques, such as Manchester encoding, of a digital signal at a relatively high bit rate, for example, 10 megabits per second. The receiver portion of the ETHERNET transceiver recovers the clock signal from the serial data, then extracts the serial data.

According to the present invention, a protocol is used that is self-timing and is capable of being transmitted at relatively high data rates. In a preferred embodiment of the present invention, the ETHERNET ISO/IEC 8802.3 standard, similar to the IEEE 802.2 standard, has been chosen because of these requirements and, in part, because it is well-known, and as such easily adapted to the present invention. It should be appreciated that other protocols and encoding techniques may be employed depending upon the particular application in which the invention is to be used.

Figure 2:
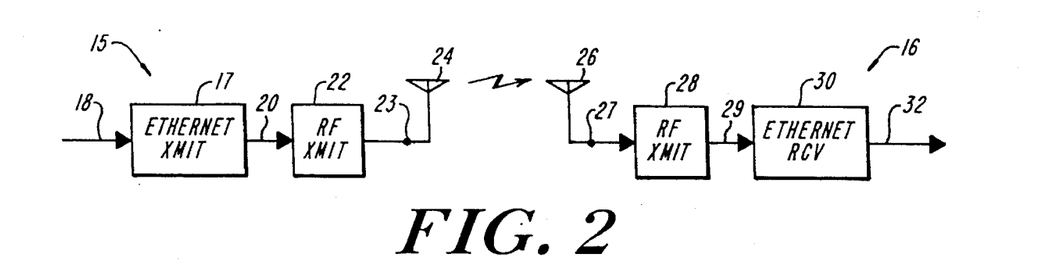
FIG. 2 is a schematic diagram of a mechanically non-contacting communications system of the present invention.

Referring to FIG. 2, the invention includes a non-contacting (i.e., in the mechanical sense) communications link having an encoder-transmitter 15 and a receiver-decoder 16 cooperating respectively to transmit and receive data across a spatial gap. The link of FIG. 2 can be implemented using any mechanically non-contacting communications technique, such as an optical or radio frequency technique, including infrared, ultraviolet, or any other useful frequency range of the electromagnetic spectrum. Moreover, capacitive or inductive coupling can be utilized. In a preferred embodiment of the invention, radio frequency (RF) capacitive coupling is employed. In an alternate preferred embodiment, near field transmission is employed, using a near field antenna assembly.

In a further preferred embodiment of the invention, the encoder-transmitter 15 includes an encoder, such as an ETHERNET transceiver 17 configured to transmit only, for providing an encoded digital signal 20 representative of a digital input data signal 18 in accordance with ETHERNET protocol. A transmitter, such as a radio frequency (RF) transmitter 22, receives the encoded digital signal 20 from transceiver 17, and provides an analog RF signal 23, representative of the encoded signal 20, to transmitting antenna assembly 24 of the encoder-transmitter. The receiver-decoder includes a receiving antenna assembly 26, disposed at a distance from the transmitting antenna assembly 24, for detecting the analog RF signal 27, and providing it to an RF receiver 28 of the receiver-decoder. The RF receiver 28 provides a digital encoded signal 29, to an ETHERNET transceiver 30 of the receiver-decoder, transceiver 30 being configured to receive only. The ETHERNET transceiver 30 then decodes the encoded signal 29, thereby providing a digital output data signal 32 that is the same as the digital input data signal 18 in terms of its information content.

Figure 3:
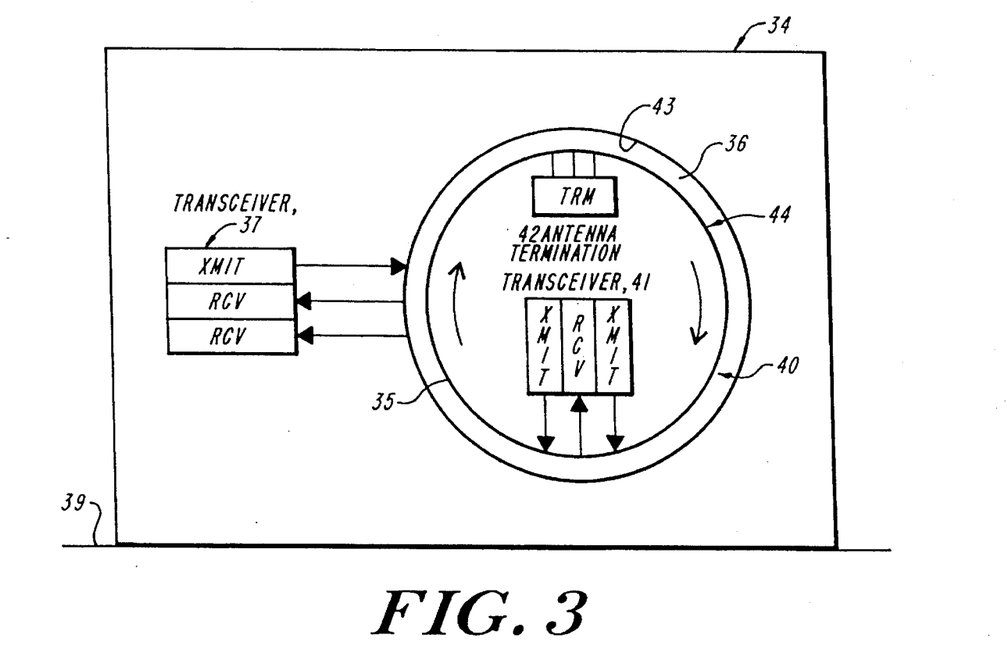
FIG. 3 is a schematic cross-sectional view of a second device rotatably disposed within a first device and utilizing the communication system of the present invention.

FIG. 3 shows, schematically and in cross-section, a first device 34 having an opening 36 for receiving a second device 44. The first device is preferably stationary with respect to a supporting surface 39. A stationary transceiver assembly 37 is fixed relative to the first device 34. The second device 44 is supported within the opening 36 so that it is rotatable about a rotation axis (normal to the view plane of FIG. 3) and forms within the opening 36 an annular air gap, indicated at 40; between the outer periphery 35 of the rotatable device 44 and the inner circumference 43 of the opening 36. A rotatable transceiver 41 is fixed relative to and rotates with the second device 44.

In a preferred embodiment, it is desirable that more information (approximately twice as much) be transmitted from the rotatable device 44 to the stationary device 34 than transmitted from device 34 to device 44 so that the transceiver assembly 37 of the first device 34 includes two receivers for simultaneously receiving two data signals, and only one transmitter for transmitting one data signal. The rotatable device 44 preferably includes a second ETHERNET transceiver assembly 41 that is complementary to the first transceiver assembly 37 in that, for each transmitter of the first transceiver assembly 37 there is a respective receiver in the second transceiver assembly 41, and for each receiver of the first transceiver assembly 37 there is a respective transmitter in the second transceiver assembly 41. Preferably, each receiver of transceiver assemblies 37 and 41 includes an RF receiver 28 as shown in FIG. 2 that receives an RF signal 27 and provides an encoded digital signal 29, and an ETHERNET receiver 30 that receives the encoded digital signal 29 and provides a decoded digital data signal 32. Similarly, each transmitter of the transceiver assemblies 37 and 41 includes an ETHERNET transmitter 17 that receives a digital data signal 18, such as a digital data signal from a computer, and provides an encoded digital signal 20 and an RF transmitter that transmits an RF signal 23 representing the encoded digital signal 20.

As will be more evident hereinafter, each transmitter and receiver of the rotatable transceiver assembly 41 includes an antenna assembly, generally disposed around the periphery 35 of the rotating device and terminating in its characteristic impedance at 42, preferably 180° opposite where the corresponding transmitter or receiver is connected. An antenna assembly for each of the transmitter and receivers of the transceiver assembly 37 is fixed relative to stationary device 34 within the air gap 36 at a fixed distance from the corresponding antenna assembly on periphery 35 of the rotating device 44 (so that the spacing between the two antenna assemblies remains substantailly constant as the rotating device 44 rotates) and also terminates at each end with its characteristic impedance. The stationary antenna assembly extends around the periphery of rotating antenna through a predetermined arc sufficiently large so that as the terminated ends of the antenna 35 at 42 rotate past the stationary antenna assembly, data can still be transferred between the two assemblies so that data transfer can occur at any angular position of the rotatable device 44.

Thus, in the present embodiment, data is communicated through air gap 36 from the transmitter of the transceiver assembly 37 of stationary device 34 to the receiver of transceiver assembly 41 of the rotatable device 44 using one transmitter/receiver pair, and data is communicated from the two transmitters of assembly 41 of rotatable device 44 to the corresponding receivers of the assembly 37 of the stationary device 34 using two transmitter/receiver pairs. Therefore, as the terms are used herein, there are two "down link" channels and one "up link" channel. Consequently, in a preferred embodiment, data can be transferred from the rotatable device 44 to the stationary device 34 at twice the rate that data can be transferred to the rotatable device 44 from the stationary device 34. This embodiment is especially useful when a computer system is affixed to the rotating device 44 for extensive data acquisition, such as image data acquisition system of a CT scanner, and must transmit the image data to a stationary computer system fixed relative to supporting surface 39, and the stationary computer provides a lesser amount of control and system diagnostic data to the rotating computer system.

Figure 4:
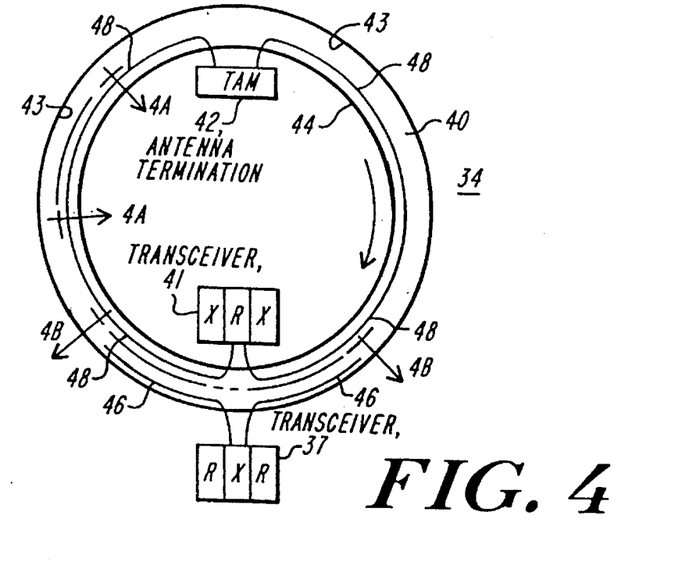
FIG. 4 is a more detailed schematic cross-sectional view of the rotatable device having an antenna assembly disposed about its periphery and rotatable within an aperture of a stationary device having a stationary antenna disposed therein.
Figure 4A:
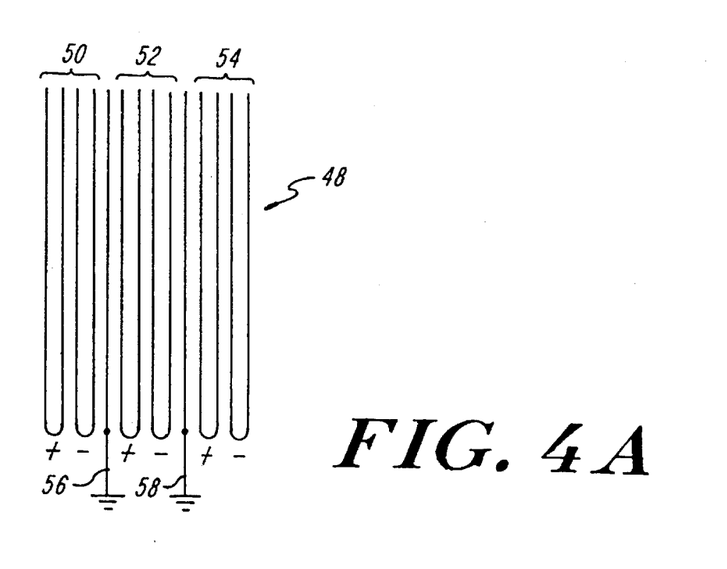
FIG. 4A is a schematic side view depicting a rotating set of micro-strip conductors disposed about the circumference of the rotatable device of the apparatus shown in FIG. 4.
Figure 4B:
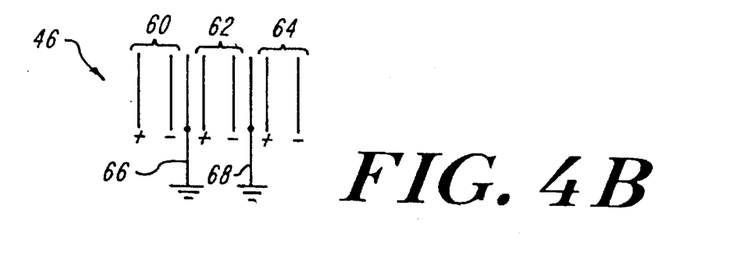
FIG. 4B is a schematic side view depicting a stationary set of micro-strip conductors fixed relative to the stationary device and capacitively coupled to the conductors of the rotating device.

As shown in greater detail in FIGS. 4, 4A and 4B, preferably, stationary antenna assembly 46 for the stationary device 43 is provided in the form of a set of micro-strip conductors 60, 62, 64, 66 and 68 (seen schematically in FIG. 4B) electrically connected to the stationary transceiver assembly 37, while a rotatable antenna assembly 35 for the rotatable device 44 is provided in the form of a set of micro-strip conductors 50, 52, 54, 56 and 58 (seen schematically in FIG. 4A) electrically connected to rotatable transceiver assembly 41. The micro-strips 60, 62, 64, 66 and 68 of the stationary antenna assembly 46 are fixed relative to the surface 43 forming the outer surface of air gap 40 so as to be precisely spaced from the rotatable micro-strip conductors of assembly 48 as the rotatable device rotates about its axis. The stationary micro-strip conductors 60, 62, 64, 66 and 68 of antenna assembly 46 are each connected to the transceiver 37 so as to form a two pole antenna (i.e., the transceiver is connected to the center of each strip 60, 62 and 64), and each are of a length (from end to end) that is less than one quarter of the wavelength of the highest transmission frequency of any signal transmitted to or received from the rotating device 44 so that coupling between the two antenna assemblies is capacitive. For example, when the highest frequency transmitted is about 480 MHz, the end-to-end length of each micro-strip conductor 60, 62 and 64 of assembly 46 is no more than about 300 mm, although smaller lengths are preferred. The fixed micro-strip conductors 60, 62, 64, 66 and 68 of antenna assembly 46 preferably lie on a curved surface which preferably has a center of curvature coincident with the rotation axis of the rotatable device so as to lie along an arc which extends coincident with and preferably lies within the air gap 40 so that the distance between the micro-strip conductors of the stationary antenna assembly and the micro-strip conductors of the rotatable antenna assembly is substantially constant around the entire circumference of the stationary antenna assembly.

In a preferred embodiment, the micro-strip conductors 60, 62, 64, 66 and 68 of stationary antenna assembly 46 are realized as conductive traces on a printed circuit board, while the rotating micro-strip conductors 50, 52, 54, 56 and 58 of rotatable assembly 48 are disposed on a flexible ribbon.

As will be apparent hereinafter, the micro-strip conductors 60, 62, 64 are each provided as a set of two strips, while micro-strip conductors 50, 52 and 54 are each provided as a group of four strips, with each set and group being differentially driven, while micro-strip conductors 66, 68, and 56 and 58 are grounded. All of the micro-strip conductors are active transmission lines disposed over a continuous ground plane, the transmission lines having a characteristic impedance of, for example, 50 ohms.

The micro-strip conductors 50, 52, 54, 56 and 58 of assembly 46 of the rotatable device 44 are circumferentially arranged around both sides of the periphery 35 of the rotatable device 44 from the location of the transceiver assembly 41 and terminating 180° therefrom as indicated at 42. Thus, half of each of the rotating micro-strip conductors 50, 52, 54, 56 and 58 of antenna assembly 48 are disposed along a first half of the outer periphery 35 of the rotatable device 44, and the remaining half of each of the rotating micro-strip conductors are disposed along a second half of the outer periphery 35 of the rotatable device 44, ensuring that the signal strength transmitted between the two assemblies 46 and 48 remains substantially constant throughout a complete revolution of the rotatable device 44.

In applications where extremely low error rates are required, such as medical diagnostic equipment, e.g., CT scan apparatus, cross talk between data channels must be minimized. Referring to FIG. 4A, the three pairs of conductors 60, 62 and 64, are used with a corresponding group 50, 52 and 54 so as to define three separate data transmission channels. To reduce cross talk between the channels, the conductor groups 50 and 52 are separated by a first grounded guard conductor 56, and the conductor groups 52 and 54 are separated by a second grounded guard conductor 58. Similarly, the conductor pairs 60 and 62 are separated by a grounded guard conductor 66, and the conductor pairs 62 and 64 are separated by a grounded guard conductor 68.

To further reduce cross talk, the groups 50 and 54, used for transmitting signals respectively to the conductor pairs 60 and 64 so as to define the two down-link channels, are driven at one or more drive frequencies within a first frequency range $f_1$, and the conductor pair 62 used for transmitting signals to the group 52 so as to define the up link channel, are driven at one or more drive frequencies within a second frequency range $f_2$ which is outside of, and preferably less than the frequency range $f_1$. Disposing the conductor group 52 of the up link channel between the conductor groups 50 and 54 of the respective down link channels further reduces cross talk by increasing the spatial separation between lines driven at the same frequency, thereby exploiting the FM capture effect. Thus, for example, the frequency range $f_1$ can fall generally within the range of 130–230 MHz, and the range $f_2$ can fall generally within the range of 320–470 MHz. The driving frequencies of the second frequency range $f_2$ are preferably chosen so as to be coincident with null frequencies associated with the first frequency range $f_1$, thereby further reducing cross talk, where the null frequencies associated with the first frequency range depend on the first frequency range $f_1$, and the range $f_1$ is chosen so as to provide a null spacing that is substantially coincident with the spacing of the conductors within a strip line cable that includes the pairs 50, 52, and 54.

In a preferred embodiment, data transmitted over the two down link channels is packetized in accordance with the ETHERNET protocol identified above, so that each packet includes addressing information. Thus, even if cross talk occurs between the two down link channels, data can be delivered to its intended address.

Having two down link channels, data can be sometimes carried simultaneously over the two down link channels, and sometimes alternately carried over one down link channel or the other down link channel. In order to further minimize cross talk, the two down link channels preferably are time-multiplexed such that the amount of time that data is simultaneously carried over the two down link channels is small relative to the time that data is alternately carried over one down link channel or the other down link channel. For example, the percent of time that data is simultaneously carried over the two down link channels is advantageously only about one percent. Preferably, only synchronization data is transmitted during the period of channel transmission overlap, while other critical data, such as image data, is transmitted only when a single channel is active.

To minimize radiative losses, the four conductors of each of the outer groups of micro-strip conductors 50 and 54 are differentially driven in pairs (+—), i.e., a first pair of the four conductors (the + conductors of each pair 50 and 54) is driven in opposite phase with respect to a second pair of the four conductors (the − conductors of each pair 50 and 54). Preferably, to obtain better than 20 dB rejection from symmetry, the amplitude of the oppositely phased signals must be equal to within about 5%. Additionally, in a preferred embodiment, to further reduce radiated power, the transmitter power is limited to about 20 mW or less (e.g., 1 V RMS 50 ohm).

In a manner well known in the art, a balun transformer (not shown) is used to drive each of the conductors 50, 54 and 62 when transmitting a signal through the respective transmitting channel so as to match the impedance of the conductors to the impedance of the transmitter of the respective transceiver that drives them, thereby enhancing power transfer between the transmitter and the receiving conductors. The receiving conductors 52, 60 and 64 are driven by oppositely phased RF signals provided from the transmitting conductors 62, 50 and 54, respectively. These receiving conductors are also connected through a balun transformer (not shown) to the respective receiver of the corresponding transceiver.

With reference to FIG. 4B, the stationary groups of micro-strip conductors 60, 62 and 64 of the antenna assembly 46 are cooperative with the respective rotating set of micro-strip conductors 50, 52 and 54 of the antenna assembly 48. The assembly 46 includes three groups of conductors 60, 62, and 64, disposed close enough to the respective rotating micro-strip conductors 50, 52 and 54 of the assembly 48 to ensure good electrical coupling thereto, and far enough to accommodate mechanical tolerances of the rotating device 44 and the stationary device 34 so that the two never mechanically contact one anther. Further, each of the micro-strip conductors is sufficiently wide so as to maintain coupling throughout rotation of the rotatable device 44 and during out of plane motion (e.g., nutation) of the rotatable device 44.

Figure 5:
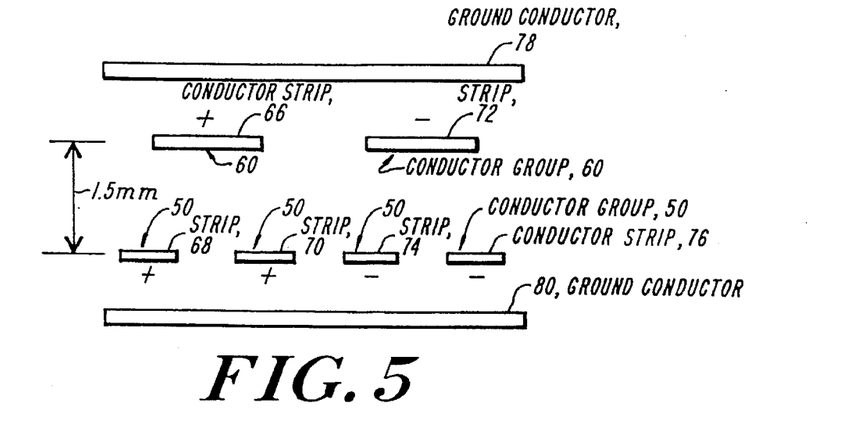
FIG. 5 is a cross-sectional view of the normal operating position of four rotating micro-strip conductors cooperative with two stationary micro-strip conductors, and their associated ground planes.

Referring to FIGS. 4B and 5, it is seen that each of the differential pair of the conductor groups 50, 52 and 54 is actually formed as a loop so that, for example, the + pair of conductors of group 50, includes + strips 68 and 70 connected at their ends through their characteristic impedances at termination point 42 to ground. The corresponding pair of conductors 60, 62 and 64 (60 being shown in FIG. 5) is provided as one + strip 66 and one − strip 72, respectively disposed between and spaced from strips 68 and 70 and from strips 74 and 76. In a normal position strips 66 and 72 of each of the differential pairs of conductor groups 50, 52 and 54 are radially spaced from strips 68, 70, 74 and 76 of each of the pairs of conductors 60, 62 and 64 by a predetermined amount, e.g., 1.5 mm, so as to provide capacitive coupling with good RF transmission and reception at the various driving frequencies and power levels of the transmitted signals. In the preferred embodiment, the ground conductor 78 is incorporated into the printed circuit board supporting conductors 60, 62 and 64, while the ground plane conductor 80 is incorporated into the flexible ribbon supporting conductors 50, 52 and 54, wherein a layer of insulation separates the micro-strip conductors from the corresponding ground plane conductor. The ground planes 78 and 80 provide electromagnetic shielding.

Although the dimensions of the micro-strip conductors can vary depending upon the particular application, in the preferred embodiment, the length of each of the micro-strip conductors 50, 52, 54, 56 and 58 is about 2 meters. The width of the micro-strip conductors 50, 52, 54, 56 and 58 are about 1.57 mm, while micro-strip conductors 60, 62, 64, 66 and 68 are about 2.5 mm wide. While the radial separation between the stationary and rotating micro-strip conductors in the preferred embodiment is 1.5 mm, the spacing can vary from about 0.5 mm to about 2.5 mm as the device 44 rotates about its axis, without degrading signal transmission between the stationary and rotating devices 34 and 44. Similarly, the rotating device 44 can laterally move out of its rotation plane with respect to the stationary device 34 by about ±1.0 mm.

Figure 5A:
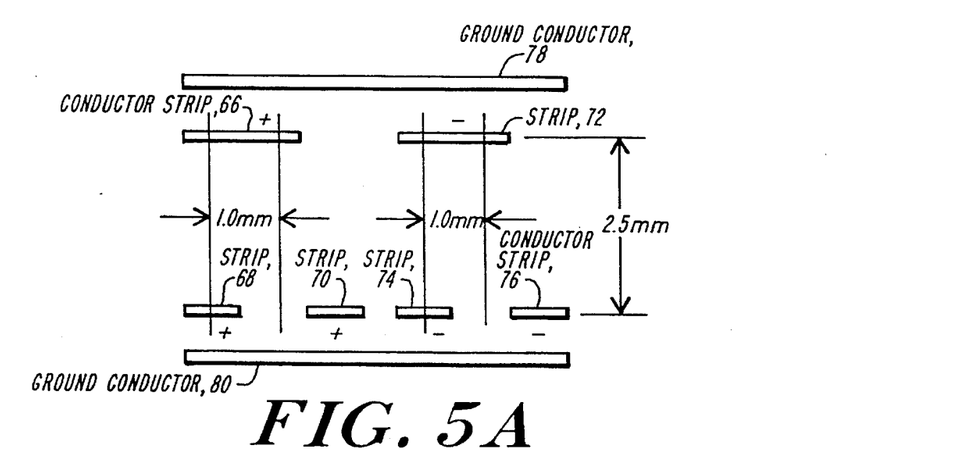
FIGS. 5A, 5B, 5C, and 5D are cross-sectional views of four operating position extreme of the rotating micro-strip conductors relative to the stationary micro-strip conductors of FIG. 5.
Figure 5B:
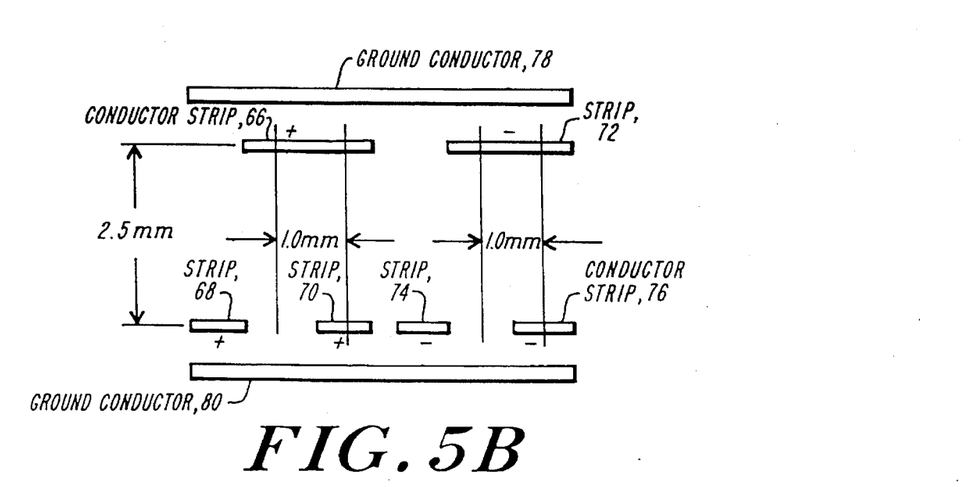
Figure 5C:
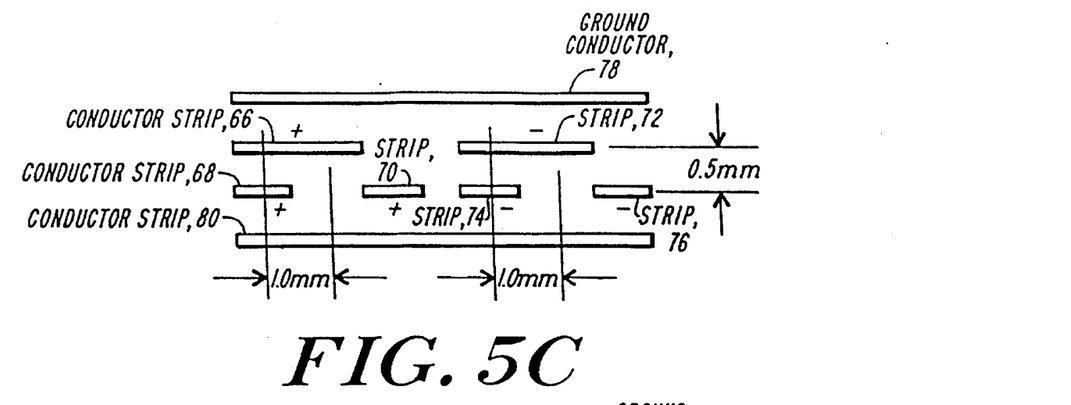
Figure 5D:
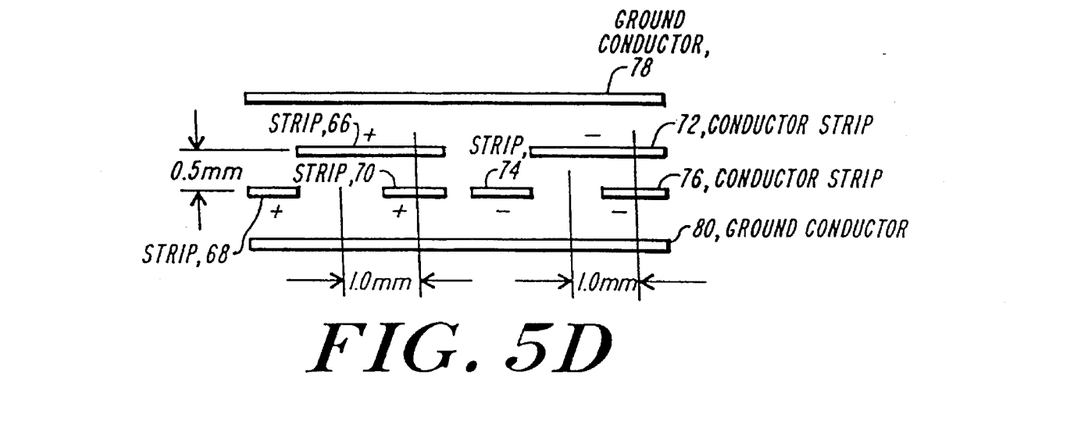

FIGS. 5A, 5B, 5C, and 5D each represent a different combination of radial and lateral out of plane displacement, showing how proximity can vary, for example, from about 0.5 mm to about 2.5 mm, as can be seen by comparing FIG. 5A with FIG. 5C, or FIG. 5B with FIG. 5D, while at the same time, lateral out of plane displacement can vary, for example, by about 1.0 mm, as can be seen by comparing FIG. 5A with FIG. 5B, or FIG. 5C with FIG. 5D.

Figure 6:
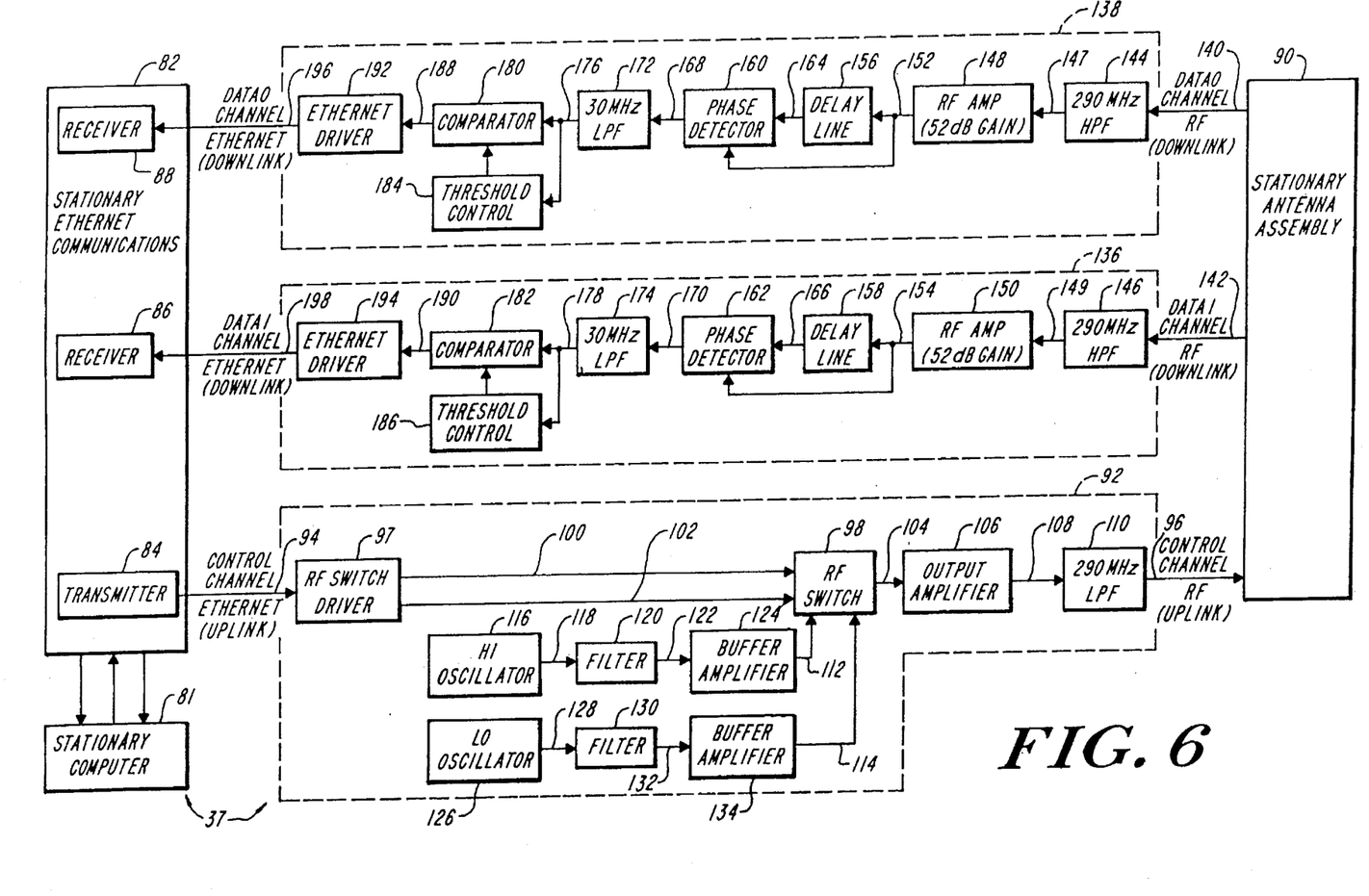
FIG. 6 is a block diagram of two RF receivers and an RF transmitter cooperative with a stationary antenna assembly and a stationary ETHERNET communications board.

FIG. 6 shows in detail the stationary transceiver assembly 37 of FIG. 4, including a transmitter and two receivers. More specifically, a stationary computer 81 is connected to an ETHERNET communications board 82 that includes an ETHERNET transceiver 84 set to transmit, and two ETHERNET transceivers 86 and 88 set to receive. The stationary antenna assembly 90 includes the stationary set of microstrip conductors 46 (of FIG. 4B), as previously described. An RF transmitter 92 is responsive to an ETHERNET level encoded data signal 94 provided from the transmitter 84, and provides a frequency shift key (FSK) RF signal 96 representative of the signal 94 to the stationary antenna assembly 90. In alternate embodiments, other modulation techniques can be used, such as phase modulation and spread spectrum modulation.

The RF transmitter 92 includes an RF switch driver 97 which provides two output driving signals 100 and 102 which are always inverted with respect to one another. When the ETHERNET level encoded data signal 94 is in a high state, for example, driving signal 100 is high while driving signal 102 is low. Conversely, when signal 94 is in a low state driving signal 100 is low while driving signal 102 is high.

For example, the ETHERNET signal can transition between 0 and −2 volts at 10 megabits a second, while the driving signals 260 and 264, and 262 and 266 transition between 0 and −5 volts. The two signals 100 and 102 are used to respectively drive two RF switches, such as a Gallium Arsenide RF switches, of a RF switch module 98. The switches are designed to close when the state of the respective drive signal is of a certain state, such as high so that one of the switches is always closed and one always open depending upon the state of the ETHERNET level encoded data signal 94. Two filtered and amplified signals 112 and 114 each of a different frequency are applied to each of the switches of switching module 98, so that the FSK signal 104 provided at the output of switch 98 is of one frequency when the ETHERNET level encoded data signal 94 is of one state (high) and is of a different frequency when signal 94 is of an opposite state (low). In order to generate the FSK signal 104 at the two frequencies, two separate oscillators are provided, one the HI oscillator 116, set at a high frequency, the other the LO oscillator 126, set at a lower frequency.

In a preferred embodiment, the HI oscillator 116 is a standard TTL oscillator that provides a plurality of harmonics, where the third harmonic is a 210 MHz signal 118 that is selected by a bandpass filter 120. A filtered signal 122 provided by the filter 120 is amplified by a buffer amplifier 124 that isolates the oscillator 116 from the RF switch 98 so as to produce drive signal 112 that is applied to RF switch 98. The LO oscillator 126 is also preferably a standard TTL oscillator that provides a signal 128 having a plurality of harmonics including a third harmonic signal 132 at 138 MHz, which is selected by a bandpass filter 130. The filtered signal 132 is amplified by a buffer amplifier 134 that isolates the oscillator 126 from the RF switch 98 so as to provide drive signal 114 that is applied to RF switch module 98. The RF switch module 98 provides an FSK signal 104 to an output amplifier 106 so as to produce an amplified FSK signal 108 to a 270 MHz low pass filter 110. The filter 110 provides a filtered and amplified FSK RF signal 96 to the stationary antenna assembly 90 for transmission. Signal 90 is preferably about 20 milliwatts; although this can clearly vary depending upon the design of the antenna assemblies and the dimensions of the air gap 40.

FIG. 6 also shows two RF receivers 136 and 138. The stationary antenna assembly 90 provides FSK RF signals 140 and 142, each of which, as will be more evident hereinafter, contains two frequency components, respectively representative of the high and law states of the ETHERNET level encoded signal and well above 290 MHz. The FSK RF signals are applied respectively to high pass filters 144 and 146 (290 MHz) which remove cross-talk from the up link signal provided on the up link channel. Filtered signals 147 and 149 are respectively provided from the outputs of filters 144 and 146 and applied to the corresponding RF amplifiers 148 and 150 each having, for example, 52 dB gain. The amplified signals 152 and 154 are provided to corresponding delay lines 156 and 158 and to phase detectors 160 and 162. The outputs of lines 156 and 158, delayed signals 164 and 166 are also provided to the respective phase detectors 160 and 162. The phase detectors 160 and 162 cooperate with the corresponding delay lines 156 and 158 so as to FSK demodulate the corresponding signals 152 and 154. The delay lines 156 and 158 are chosen according to the lower frequency of the pair of FSK frequencies of each signal, so the phase difference will be 0 degrees at the lower frequency and therefore the output of the detector will be at its most negative voltage level (a logic low signal). At the higher frequency, the phase difference will be 180 degrees, and the output of the detector will be at its most positive (a logic high signal). Alternatively, the phase detectors 160 and 162 each provide a negative voltage when its two input signals are in phase, and a positive voltage when they are out of phase. Thus, the demodulated signals 168 and 170 represent data as a sequence of high and low states which represent the sequence of frequency shifts of the amplified FSK signals 152 and 154 which in turn represent the original ETHERNET level encoded data signals received by the assembly 90. The demodulated signals 168 and 170 are then respectively provided to low pass filters 172 and 174 (e.g., 30 MHz), resulting in filtered signals 176 and 178 being provided to the corresponding comparators 180 and 182 and to threshold control modules 184 and 186, wherein each comparator cooperates with a threshold control module to normalize signal amplitude, rebalance the signal duty cycle, and correct DC signal offset, while preserving the information represented by the respective signals 176 and 178 so as to provide corrected signals 188 and 190 to the corresponding ETHERNET drivers 192 and 194. The ETHERNET drivers 192 and 194 respectively provide ETHERNET level signals 196 and 198 to the corresponding receivers 86 and 88 on the stationary ETHERNET communications board 82 for use by, for example, the stationary computer 81. Although the signals 140 and 142 may exhibit substantial phase jitter, by processing them in the manner just described such phase jitter is significantly reduced in the signals 196 and 198 that are received by the stationary ETHERNET communications board 82.

Figure 7:
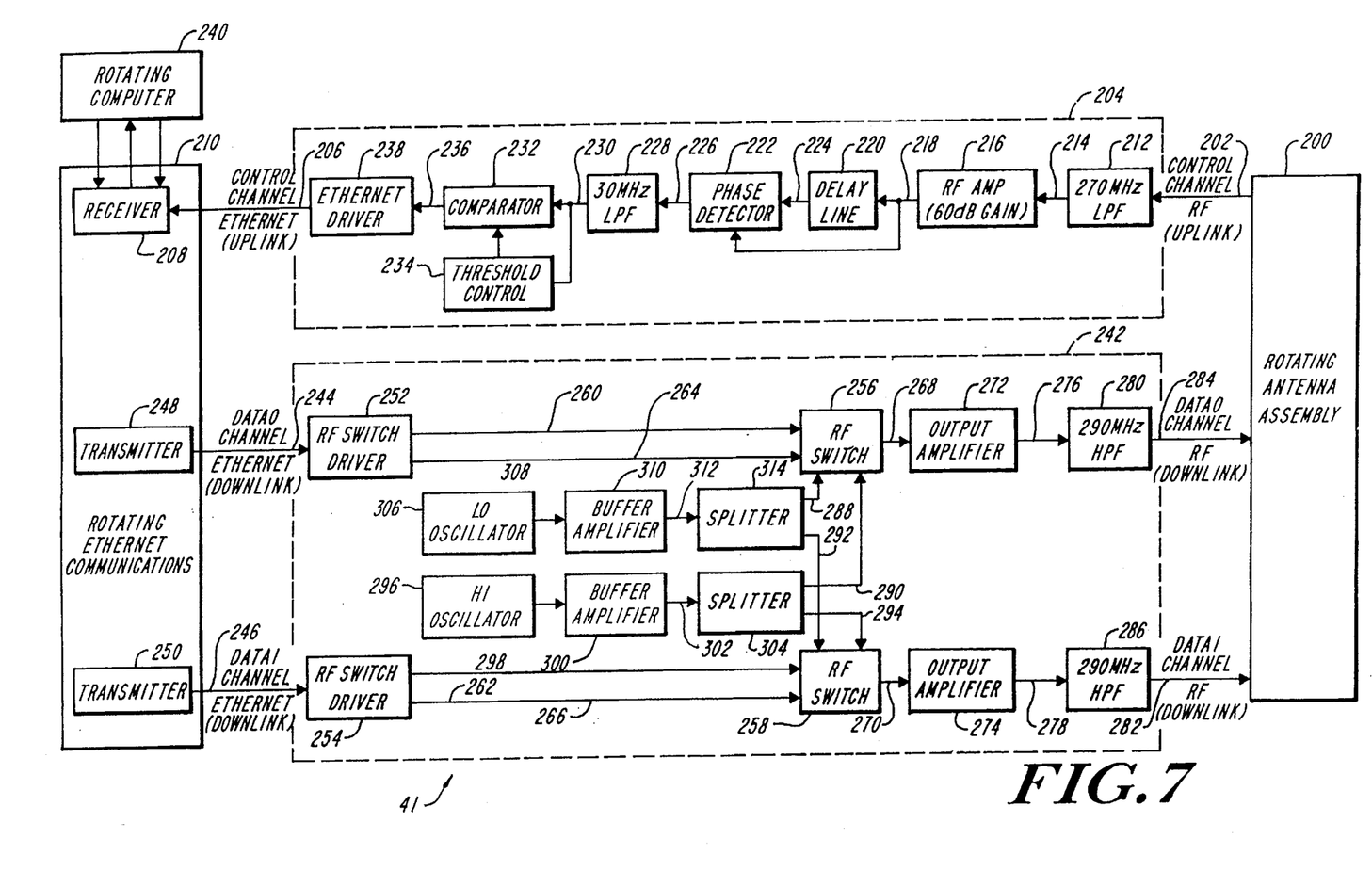
FIG. 7 is a block diagram of an RF receiver and two RF transmitters cooperative with a rotating antenna assembly and a rotating ETHERNET communications board.

Referring to FIG. 7, the rotating transceiver assembly 41 is described in greater detail. RF signals are communicated between the stationary antenna assembly 90 (not shown in FIG. 7) and the rotating antenna assembly 200 so that an FSK RF signal 202 (essentially signal 96 of FIG. 6 transmitted by the antenna assembly 90) is received by the rotating antenna assembly 200, and converted into an ETHERNET level signal 206 by an RF receiver 204 for use by an ETHERNET receiver 208 on a rotating ETHERNET communications board 210. Conversion of the FSK RF signal 202 into the ETHERNET level signal 206 is accomplished in essentially the same manner as in the RF receivers 136 and 138 of FIG. 6.

More specifically, rotating antenna assembly 200 provides an FSK RF signal 202 which contains two frequency components, respectively representation of the high and low states of the ETHERNET signals and well above 290 MHZ. The FSK RF signals are applied respectively to a low pass filter (e.g., 270 MHZ) 212 which removes cross-talk from the down link signals provided over the down link channels. The filtered signal 214 is applied to an RF amplifier 216 having, for example, 60 dB gain. The amplified signal 218 is provided to a delay line 220 and to a phase detector 222, wherein a delayed signal 224 at the output of the delay line 220 is also provided to the phase detector 222. The phase detector 222 cooperates with the delay line 220 so as to FSK demodulate the amplified signal 218. For example, the phase detector 204 provides a negative voltage (logic low state) when its two input signals 222 and 224 are in phase with each other, and a positive voltage (logic high state) when they are out of phase. Thus, the demodulated signal 226 represents data as a sequence of two voltage levels (high and low states) which represents the sequence of frequency shifts of the amplified FSK signal 218 (as well as the original ETHERNET level encoded data signal 94 shown in FIG. 6). The demodulated signal 226 is then provided to a low pass filter 228 (e.g., 30 MHz), resulting in filtered signal 230 being provided to a comparator 232 and to a threshold control module 234, wherein the comparator 232 cooperates with the threshold control module 234 to normalize signal amplitude, rebalance the signal duty cycle, and correct DC signal offset, while preserving the information represented by signal 230 so as to provide a corrected signal 236 to an ETHERNET driver 238. The ETHERNET driver 238 provides an ETHERNET level signal 206 to the receiver 208 on the rotating ETHERNET communications board 210 for use by, for example, the rotating computer 240. Although the signal 202 may exhibit substantial phase jitter, such phase jitter is significantly reduced by the signal processing described above, before being applied to the rotating ETHERNET communications board 210.

A two-channel RF transmitter 242 is responsive to two ETHERNET level encoded data signals 244 and 246 provided by two transmitters 248 and 250 of the rotating ETHERNET communications board 210. The RF transmitter 242 provides two frequency shift key (FSK) RF signals 284 and 286, representative respectively of the signals 244 and 246, to the rotating antenna assembly 200.

The RF transmitter 242 includes two RF switch drivers 252 and 254 that drive RF switch modules 256 and 258, respectively. The modules 256 and 258 each include two RF switches, wherein the first switch is responsive to the corresponding first driving signals 260 and 262, and the second switch is responsive to the corresponding second driving signals 264 and 266 that are inverted with respect to the first driving signals 260 and 262 such that when one switch of an RF switch is open, the other switch of the RF switch is closed. For example, the ETHERNET signal 244 is a 10 MHZ signal that transitions between a 0 volts and −2 volts, and the driving signals 260 and 264 transition between 0 and −5 volts.

The RF switch modules 256 and 258 respectively provide FSK signals 268 and 270 to the corresponding output amplifiers 272 and 274 so that the amplifiers provide amplified FSK signals 276 and 278 to the 290 MHZ low pass filters 280 and 282 respectively. The filters 280 and 282 provide filtered and amplified FSK RF signals 284 and 286 to the rotating antenna assembly 200. Preferably, the signals 284 and 286 applied to antenna assembly 200 are each about 20 milliwatts; although this can clearly vary depending upon the design of the antenna assembly and the dimensions of the air gap 40.

The RF switch modules 256 and 258 respectively receive two filtered and amplified oscillator signals 288, 290 and 292, 294. In a preferred embodiment, a PLL UHF transmitter chip, such as the MOTOROLA 3240 transmitter chip, is used to generate two oscillators signals in the ultra high frequency (UHF) range, thereby serving as a HI oscillator 296 and a LO oscillator 306. The HI oscillator 296 provides a 480 MHZ signal 298 to a buffer amplifier 300 that isolates the oscillator 296 from the RF switches 256 and 258. A buffer amplified signal 302 provided by the buffer amplifier 300 is split by a splitter 304 into the two signals 290 and 294, which in turn are applied to the corresponding switches 256 and 258.

The LO oscillator 306 provides a 320 MHZ signal 308 to a buffer amplifier 310 that isolates the oscillator 306 from the RF switches 256 and 258. A buffer amplified signal 312 provided by the buffer amplifier 310 is split by a splitter 314 into the two signals 288 and 292 which in turn are provided to switches 256 and 258, respectively.

In a preferred embodiment, to further reduce jitter, the oscillators 296 and 306 receive timing information from the rotating computer 240, and the oscillators 116 and 126 receive timing information from the stationary computer 81.

The preferred embodiment of each of the transmitters 92 and 242 is characterized as having an input signal provided by an ETHERNET transmitter in accordance with Standard ISO/IEC8802-3 (ethernet) P.L. (10 Base 5). The transmitters have an output signal of 7 dBm±3 dBm. Power consumption is less than 2.5 Watts per channel using a +12 v line. Jitter introduced by a transmitter is less than 8 nanoseconds. In addition, the preferred receivers 136, 138, and 204, each is characterized as having an input signal in the range of −10 dBm to −50 dBm, and an output signal in accordance with ISO/IEC 8802-3 (ethernet) P.L. Power consumption is less than 2.5 Watts per channel using a +12 volt line. Jitter introduced by a receiver is less than 6 nanoseconds.

Figure 8:
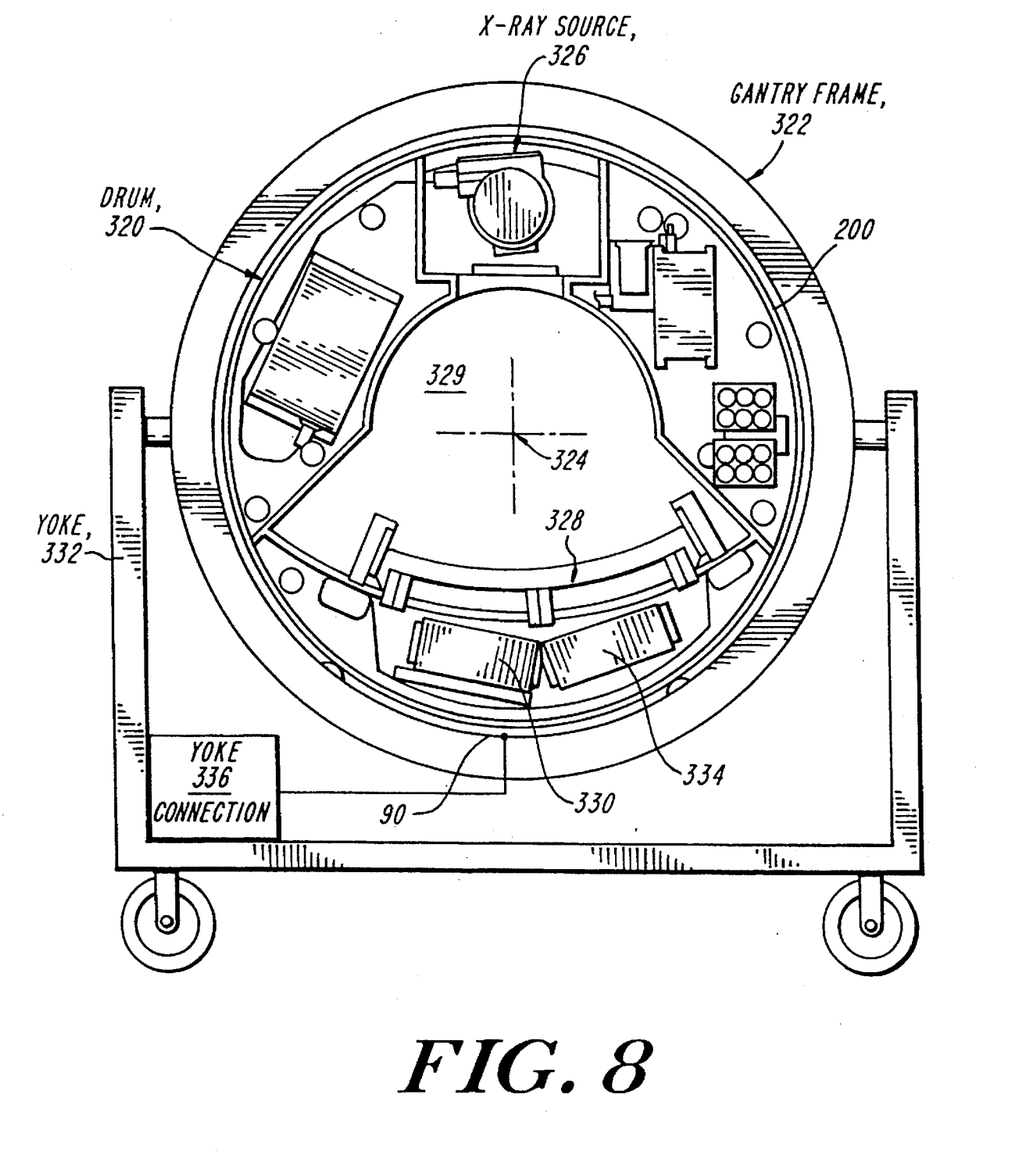
FIG. 8 is an end view of a CT scanner modified to include the present invention.

To further illustrate a possible use of the apparatus of the invention, in FIG. 8 a typical CT scanner has been modified to include the present invention. As shown, a drum 320 is rotatably supported in a gantry frame 322 for rotation about an axis 324. A source 326 of X-rays and a detector array 328 are disposed on opposite sides of an opening 329 adapted to receive the object to be scanned. A data acquisition system 330 is also provided on the drum 320 for acquiring image data provided by detectors of array 328 during a scan. An on board computer 240 is mounted on the drum. The gantry frame 322 is supported in a yoke 332 which is also used to support the stationary computer 81.

In accordance with the present invention, the rotating antenna assembly 200, is preferably mounted around the perimeter of the drum in a manner as previously described. The ETHERNET communications board 210, RF receiver 204 and RF transmitters 242 are suitably mounted on the drum, (as generally indicated at 334 in FIG. 8) and connected to computer 240 and antenna assembly 200 in the same way as described in FIG. 7. The stationary antenna assembly 90 is secured to the frame in proximity to the rotating antenna assembly 200, as previously described in connection with FIG. 6. The ETHERNET communication board 82, RF receivers 136 and 138, and the RF transmitter 92 are suitably fixed relative to the yoke, as generally indicated at 336, in FIG. 8, and connected to computer 81.

Upon receiving control data, the detector array 326 provides data to the data acquisition system 330. The data is provided to rotating computer 240. In addition, other data associated with the lateral movement of the drum within the rotational plane of the drum, can also be sensed by detectors (not shown) and compensation data can be generated along with the imaging data. Such a system is shown and described in U.S. patent application Ser. No. 08/162,653, entitled APPARATUS FOR AND METHOD OF MEASURING GEOMETRIC, POSITIONAL AND KINEMATIC PARAMETERS OF A ROTATING DEVICE filed in the names of Bernard M. Gordon, Douglas Abraham, David Winston and Paul Wagoner on Dec. 6, 1993 and incorporated herein by reference, which was abandoned in favor of continuing U.S. patent application Ser. No. 08/338,263 filed Nov. 10, 1994 and issuing as U.S. Pat. No. 5,432,339 on Jul. 11, 1995, entitled "Apparatus For and Method of Measuring Geometric, Positional and Kinematic Parameters of a Rotating Device Having a Plurality of Interval Markers". The movement compensation data is used to compensate for variations, vibrations, and imperfections in the rotational motion of the rotating device 44 so as to provide image data of a quality that more closely approximates image data collected by a geometrically perfect and rotationally stable rotating device. After data acquisition, data collected from the detector array is merged with compensation data, the merged data then being transmitted via the two time-multiplexed down-link channels.

Thus, measurement and control data is transmitted from the drum 320 to the stationary computer 81 via the two time-multiplexed down-link channels so as to provide high speed data transfer. It is necessary to employ two down link channels when data is generated or acquired at a rate that exceeds the capacity of a single channel, such as in some CT scan applications. In the preferred embodiment, the data rate of a single channel is determined by the capacity of an ETHERNET transceiver, which is 10 megabits per second in the presently described embodiment.

The computer 81 checks the merged data for integrity upon its receipt. The measurement data is then extracted from the merged data for further processing. In a CAT scan system, for example, the measurement data is used in a back projection process.

To further illustrate the apparatus of the invention, the stationary computer 81 generates control information at a rate of 0.1 Mbyte per second represented by, for example, a sequence of 64-byte data blocks every 700 microseconds, and this control information is transmitted by the transmitter 84 on the stationary ETHERNET communications board 82 to the RF transmitter 92 and stationary antenna assembly 90 for reception by the rotating antenna assembly 200, the RF receiver 204, and the ETHERNET receiver 208, for use by the rotating computer 240 on the rotating device 40. The control information thus transmitted and received is generated and used in real-time. Upon receipt of a data block, data is acquired by a data acquisition system (not shown) on board the rotating device 40, and the information conveyed by the data block is used to control other subsystems (not shown) on board the rotating device 40.

The data acquisition system on board the rotating device 40 generates data for transmission to the stationary device at a rate of approximately 1.2 Mbytes per second as a sequence of 800-byte data blocks every 700 microseconds.

Other modifications and implementations will occur to those skilled in the art without departing from the spirit and the scope of the invention as claimed. For example, the data communication systems described can be easily implemented for transferring data between two devices which move relative to one another, but not necessarily rotationally about a rotation axis. For example, a device, such as a train, that moves over a linear track can be provided with a transceiver assembly 37 and an antenna assembly similar to assembly 46 except flatten so as to travel in a plane parallel to the plane of the track, and the track provided with the transceiver 42 and the antenna assembly similar to assembly 48, except flattened to follow the track. Accordingly, the above description is not intended to limit the invention except as indicated in the following claims.

What is claimed is:

1. An apparatus for simultaneously bidirectionally transferring data between a first device and a second device mounted for rotation with respect to the first device, the apparatus comprising:

a first antenna assembly fixed relative to the first device;

a second antenna assembly sufficiently disposed around the periphery of and fixed relative to said second device such that said first antenna assembly and said second antenna assembly are in communicating relationship substantially throughout an entire revolution of said second device, and so that a spatial gap is provided between said first and second antenna assemblies; and data transfer means for simultaneously bidirectionally transferring data between said first and second antenna assemblies as said second device rotates relative to said first device, said data transfer means comprising means for transmitting data from said first device to said second device through at least one data transmission channel, means for transmitting data from said second device to said first device through at least one additional transmission channel, and means for isolating said data transmission channels so as to minimize cross talk between said data transmission channels.

2. Apparatus according to claim 1, wherein said first and second antenna assemblies are capacitively coupled to one another.

3. Apparatus according to claim 1, wherein said means for transferring data includes a first transceiver assembly coupled to said first antenna assembly, and a second transceiver assembly coupled to said second antenna assembly so that said transmission channels are established between said first and second transceiver assemblies.

4. Apparatus according to claim 1, wherein said means for transmitting data from said second device to said first device transmits said data through at least additional two data transmission channels separate from the data transmission channel used to transmit data from said first device to said second device, and wherein said means for isolating said data transmission channels includes means for transmitting data through the data transmission channels used to transmit data from said second device to said first device across the spatial gap at two predetermined locations, and means for transmitting data through the data transmission channel used to transmit data from the first device to the second device across the spatial gap at a third predetermined location between said two predetermined locations.

5. Apparatus according to claim 4, wherein said means for transmitting data through the two data transmission channels used to transmit data from said second device to said first device includes means for multiplexing said data through the two data transmission channels.

6. Apparatus according to claim 1, wherein said means for isolating said channels so as to minimize cross talk comprises means for transmitting data from said second device to said first device as a first data signal at a first frequency, and means for transmitting data from said first device to said second device as a second data signal at a second frequency different from said first frequency.

7. Apparatus according to claim 1, wherein said second antenna assembly includes, for each of said channels, at least two of conductive strips spaced apart from one another and extending around the periphery of said second device, and said first antenna assembly includes, for each of said channels, at least two conductive strips spaced apart from one another and extending through a predetermined angle about the periphery of said second device, wherein the conductive strips of one of said assemblies opposes corresponding conductive strips of the other assemblies so as to define said spatial gap.

8. Apparatus according to claim 7, wherein at least one pair of said conductive strips of each of said antenna assemblies is for transmitting data associated with each of said data transmission channels, and at least one pair of said conductive strips of the other of said antenna assemblies, positioned across said spatial gap in opposition to said at least one pair of conductive strips, is for receiving said data, wherein the first pair of conductive strips used to transmit data is driven as a differential pair.

9. Apparatus according to claim 8, wherein each of said antenna assemblies includes at least one conductive strip disposed between adjacent ones of conductive strips supporting adjacent transmission channels, and said means for isolating said channels so as to minimize cross talk between said channels includes means for connecting each said at least one conductive strip to ground.

10. Apparatus according to claim 7, wherein said second antenna assembly includes, for each of said channels, at least four of said conductive strips spaced apart from one another and extending around the periphery of said second device so as to reduce cross-talk, each of said strips terminating at its opposite ends at a predetermined location in its characteristic impedance.

11. Apparatus according to claim 1, wherein said data transfer means includes:
   a first transceiver assembly coupled to said first antenna assembly;
   a second transceiver assembly coupled to said second antenna assembly; and
   means, coupled to each of said antenna assemblies, for generating an encoded data signal as a function of said data encoded in accordance with a predetermined protocol; and
   wherein each of said transceiver assemblies includes means for modulating said encoded data signal so as to produce a modulated encoded data signal for transmission across said gap, and means for demodulating said modulated encoded data signal so as to generate said encoded data signal, and means for decoding said encoded data signal in accordance with said protocol so as to produce said data.

12. Apparatus according to claim 11, wherein said means for modulating said encoded data signal includes means for modulating said encoded data signal in accordance with frequency shift keying said encoded data signal.

13. Apparatus according to claim 11, wherein said means for generating the encoded data signal, encodes the data in accordance with an ETHERNET protocol.

14. Apparatus according to claim 13, wherein ETHERNET protocol is the ISO/IEC8802-3 (ethernet) P.L. (10 Base 5) protocol.

15. An apparatus for transferring data between a first device and a second device mounted for rotation with respect to the first device, the apparatus comprising:
   a first transmitter, fixed relative to the first device, for generating a transmission signal within a first predetermined portion of the electromagnetic spectrum;
   a first receiver, fixed relative to the first device, for receiving and processing a transmitted signal within a second predetermined portion of the electromagnetic spectrum different from said first predetermined portion;
   a first antenna assembly, fixed relative to the first device and coupled to said first transmitter and first receiver, for simultaneously propagating said transmission signal and for receiving said transmitted signal;
   a second antenna assembly, fixed relative to the periphery of the second device and in sufficient mutual confronting relationship with said first antenna assembly such that said first antenna assembly and said second antenna assembly are in communicating relationship substantially throughout an entire revolution of said second device, and so as to provide a spatial gap therebetween, for simultaneously receiving said transmission signal propagated by said first antenna assembly and for propagating said transmitted signal;
   a second receiver, fixed relative to the second device so as to be rotatable therewith and coupled to the second antenna assembly, for receiving and processing said transmission signal; and
   a second transmitter, fixed relative to the second device so as to be rotatable therewith and coupled to the second antenna assembly, for generating said transmitted signal.

16. An apparatus for simultaneously and bidirectionally transferring data between a stationary device and a rotatable device that rotates with respect to the stationary device, the apparatus comprising:
   a stationary antenna assembly mounted on the stationary device;
   a stationary transceiver, mounted on the stationary device, for simultaneously transmitting and receiving signals via the stationary antenna assembly;
   a rotatable antenna assembly sufficiently mounted on the rotatable device and spaced relative to the stationary antenna such that said stationary antenna assembly and said rotatable antenna assembly are in communicating relationship substantially throughout an entire revolution of said rotatable device, and so as to provide a spatial gap therebetween so that signals can be transmitted between said antenna assemblies; and
   a rotatable transceiver, mounted on the rotatable device, for simultaneously transmitting and receiving electromagnetic signals via the rotatable antenna.

17. The apparatus according to claim 16, wherein the rotatable antenna assembly is in capacitive coupling relationship with the stationary antenna assembly.

18. The apparatus according to claim 16, wherein the rotatable antenna assembly is disposed within a near field of the stationary antenna assembly.

19. The apparatus according to claim 16, wherein the rotatable antenna assembly is mounted circumferentially about the rotatable device such that the stationary antenna assembly is in capacitive coupling relationship with the stationary antenna assembly throughout substantially an entire revolution of the rotatable device as said rotatable device rotates relative to the stationary device.

20. The apparatus according to claim 16, wherein the rotatable antenna assembly is mounted on the rotatable device around the periphery of the rotatable device such that the rotatable antenna assembly is in capacitive coupling relationship with the stationary antenna assembly throughout substantially an entire revolution of the rotatable device.

21. The apparatus according to claim 16, wherein the stationary antenna assembly includes at least one transmitting conductor for transmitting a first signal to the rotatable antenna assembly, and at least one receiving conductor for receiving a second signal from the rotatable antenna assembly.

22. The apparatus according to claim 21, wherein said stationary antenna includes a plurality of conductors, and the rotatable antenna assembly includes two conductors for use with the each corresponding conductor of the stationary antenna assembly so that data can be transferred therebetween.

23. The apparatus according to claim 21, further including means for diminishing cross talk between said at least one transmitting conductor and said at least one receiving conductor.

24. The apparatus according to claim 23, wherein said means for diminishing cross talk includes a grounded conductor disposed between said at least one transmitting conductor and said at least one receiving conductor of each antenna assembly.

25. The apparatus according to claim 16, wherein the rotatable antenna assembly includes at least one transmitting conductor for transmitting a first signal to the stationary antenna assembly, and at least one receiving conductor for receiving a second signal from the stationary antenna assembly.

26. The apparatus according to claim 25, wherein the stationary antenna assembly includes a plurality of conductors, and for each conductor of the stationary antenna assembly, the rotatable antenna assembly includes two conductors for exchanging a signal with a single conductor of the stationary antenna assembly.

27. The apparatus according to claim 25, further including means for diminishing cross talk between said at least one transmitting conductor and said at least one receiving conductor.

28. The apparatus according to claim 27, wherein said means for diminishing cross talk includes a grounded conductor disposed between said at least one transmitting conductor and said at least one receiving conductor.

29. The apparatus according to claim 16, wherein the stationary antenna assembly includes at least one transmitting conductor for transmitting a first signal to the rotatable antenna assembly, and at least two receiving conductors for respectively receiving a second signal and a third signal from the rotatable antenna assembly.

30. The apparatus according to claim 16, wherein the rotatable antenna assembly includes at least a first transmitting conductor and a second transmitting conductor for respectively transmitting a first signal and a second signal to the stationary antenna assembly, and wherein the rotating antenna assembly includes at least one receiving conductor for receiving a third signal from the stationary antenna assembly.

31. The apparatus according to claim 16, wherein the stationary antenna includes at least one transmitting conductor group for transmitting a first signal to the rotating antenna assembly, and at least two receiving conductor groups for respectively receiving a second signal and a third signal from the rotatable antenna assembly.

32. The apparatus according to claim 31, wherein each conductor group is driven differentially.

33. The apparatus according to claim 31, wherein each conductor group includes a first and second pair of conductors, the first pair being driven out of phase with respect to the second pair.

34. The apparatus according to claim 16, wherein the rotatable antenna assembly includes at least a first transmitting conductor group and a second transmitting conductor group for respectively transmitting a first signal and a second signal to the stationary antenna assembly, and includes at least one receiving conductor group for receiving a third signal from the stationary antenna assembly.

35. The apparatus according to claim 34, wherein each conductor group is driven differentially.

36. The apparatus according to claim 34, wherein each conductor group includes a first and second pair of conductors, the first pair of conductors being driven out of phase with respect to the second pair of conductors.

37. The apparatus according to claim 16, wherein the stationary transceiver includes a receiver and a transmitter, the transmitter including:

means for encoding a data signal for transmission over a computer network so as to provide an encoded data signal;

means for modulating the encoded data signal so as to provide a modulated data signal; and means for amplifying the modulated data signal for electromagnetic transmission via the stationary antenna assembly; and the receiver including:

means for detecting a modulated data signal received by the stationary antenna assembly;

means for demodulating the modulated data signal so as to provide an encoded data signal; and means for decoding the encoded data signal so as to provide a decoded data signal.

38. The apparatus according to claim 37, wherein the means for encoding is an ETHERNET transceiver.

39. The apparatus according to claim 37, wherein the means for modulating includes means for frequency modulation.

40. The apparatus according to claim 39, wherein the means for frequency modulation includes stationary means for frequency shift keying.

41. The apparatus according to claim 40, wherein the stationary means for frequency shift keying includes means for providing a first high frequency signal and means for providing a first low frequency signal.

42. The apparatus according to claim 41, wherein the rotatable transceiver includes a receiver and a transmitter, the transmitter including:

means for encoding a data signal for transmission over a computer network so as to provide an encoded data signal;

means for modulating the encoded data signal so as to provide a modulated data signal; and means for amplifying the modulated data signal for electromagnetic transmission via the stationary antenna assembly; and the receiver including:

means for detecting a modulated data signal received by the stationary antenna assembly;

means for demodulating the modulated data signal so as to provide an encoded data signal; and means for decoding the encoded data signal so as to provide a decoded data signal.

43. Apparatus according to claim 42, wherein the means for modulating of said receiver of said rotatable transceiver includes means for frequency modulation.

44. The apparatus according to claim 43, wherein the means for frequency modulation of said rotatable transceiver includes rotatable means for frequency shift keying.

45. The apparatus according to claim 44, wherein the rotatable means for frequency shift keying includes means for providing a second high frequency signal and means for providing a second low frequency signal.

46. The apparatus according to claim 45, wherein said first high frequency signal is sufficiently different from said second high frequency signal so as to significantly reduce cross talk therebetween, and wherein said first low frequency signal is sufficiently different from said second low frequency signal so as to significantly reduce cross talk therebetween.

47. The apparatus according to claim 44, wherein the means for demodulation includes stationary means for demodulating a frequency shift keyed signal.

48. The apparatus according to claim 47, wherein the stationary means for demodulating said frequency shift keyed signal includes a phase detector cooperative with a delay line.

49. The apparatus according to claim 41, wherein the means for demodulating the modulated data signal includes means for frequency demodulation.

50. The apparatus according to claim 41, wherein the means for decoding the encoded data signal includes an ETHERNET transceiver.

51. An apparatus for transferring data simultaneously bidirectionally between a first device and a second device mounted for rotation relative to the first device, the apparatus comprising:

a first computer, fixed relative to said first device, for providing a first data signal and for processing a second data signal;

a first transceiver, responsive to said first computer, for providing a first modulated transmission signal as a function of said first data signal and for simultaneously receiving a second modulated transmission signal as a function of said second data signal;

a first antenna assembly, connected to the first transceiver, for transmitting the first modulated transmission signal and for receiving said second modulated transmission signal;

a second antenna assembly for receiving the first modulated transmission signal and for transmitting the second modulated transmission signal, said second antenna assembly being fixed relative to the second device such that said first antenna assembly and said second antenna assembly are in communicating relationship substantially throughout an entire revolution of said second device and so that a spatial gap is provided between said first and second antenna assemblies;

a second transceiver, connected to the second antenna assembly, responsive to a second computer, for detecting and demodulating the first modulated transmission signal so as to provide said first data signal and for simultaneously transmitting the second modulated transmission signal as a function of the second data signal;

a second computer, fixed relative to said second device, for providing a second data signal and for processing the first data signal.

52. The apparatus according to claim 51, wherein the second computer includes means for providing a third data signal.

53. The apparatus according to claim 52, wherein the second computer includes means for time multiplexing the second data signal with the third data signal over two respective channels.

54. The apparatus according to claim 53, wherein the second data signal and the third data signal are time multiplexed such that simultaneous transmission of the second and third data signals occurs less often than alternating transmission of the second and third data signals.

55. The apparatus according to claim 52, further comprising packet means for packetizing the second data signal and the third data signals into a plurality of data packets, each data packet including address information.

56. In a CT scanner of the type including a gantry comprising a drum for supporting at least an X-ray source, and a frame for rotatably supporting the drum for rotation about a rotation axis, an apparatus for simultaneously bidirectionally transferring data between the frame and drum, the apparatus comprising:

a first antenna assembly fixed relative to the frame;

a second antenna assembly sufficiently disposed around the periphery of and fixed relative to drum such that said first antenna assembly and said second antenna assembly are in communicating relationship substantially throughout an entire revolution of said drum about said rotation axis, and so that a spatial gap is provided between said first and second antenna assemblies as said drum rotates about said axis;

means for simultaneously bidirectionally transferring data from said drum to said frame and from said frame to said drum as said drum rotates about said axis; and means for isolating the data transferred from said drum to said frame from the data transferred from said frame to said drum.

57. Apparatus according to claim 56, wherein said first and second antenna assemblies are capacitively coupled to one another.

58. Apparatus according to claim 56, wherein said means for transferring data includes a first transceiver assembly coupled to said first antenna assembly, and a second transceiver assembly coupled to said second antenna assembly.

59. Apparatus according to claim 58, wherein each of said transceiver assemblies is adapted to transmit and receive data transmitted across said gap.

60. Apparatus according to claim 59, wherein said transceiver assemblies are adapted to simultaneously transmit and receive data across said gap, said apparatus further including means for transmitting data from said frame to said drum through at least one data transmission channel, and means for transmitting data from said drum to said frame through at least one additional transmission channel, and wherein said means for isolating the data transferred from said drum to said frame from the data transferred from said frame to said drum includes means for isolating said channels so as to minimize cross talk between said channels.

61. Apparatus according to claim 60, wherein said means for transmitting data from said drum to said frame transmits said data through at least two data transmission channels separate from the data transmission channel used to transmit data from said frame to said drum, and wherein said means for isolating said data transmission channels includes means for transmitting data through the data transmission channels used to transmit data from said drum to said frame across the spatial gap at two predetermined locations, and means for transmitting data through the data transmission channel used to transmit data from the frame to the drum across the spatial gap at a third predetermined location between said two predetermined locations.

62. Apparatus according to claim 61, wherein said means for transmitting data through the two data transmission channels used to transmit data from said drum to said frame includes means for multiplexing said data through the two data transmission channels.

63. Apparatus according to claim 60, wherein said means for isolating said channels so as to minimize cross talk comprises means for transmitting data from said drum to said frame as a first data signal within a first frequency range, and means for transmitting data from said first device to said second device as a second data signal within a second frequency range different from said first frequency range, and wherein said first transceiver means includes means for filtering said first data signal so as to preclude signal energy at said second frequency range, and said second transceiver means includes means for filtering said second data signal so as to preclude signal energy at said first frequency range.

64. Apparatus according to claim 60, wherein said second antenna assembly includes, for each of said channels, at least two of conductive strips spaced apart from one another and extending around the periphery of said drum, each of said strips terminating at its opposite ends at a predetermined location in its characteristic impedance, and said first antenna assembly includes, for each of said channels, at least two conductive strips spaced apart from one another and extending through a predetermined angle about the periphery of said drum, wherein the conductive strips of one of said assemblies opposes corresponding conductive strips of the other assemblies so as to define said spatial gap.

65. Apparatus according to claim 64, wherein at least one pair of said conductive strips of each of said antenna assemblies is for transmitting data associated with each of said data transmission channels, and at least one pair of said conductive strips of the other of said antenna assemblies, positioned across said spatial gap in opposition to said at least one pair of conductive strips, is for receiving said data, wherein the first pair of conductive strips used to transmit data is driven as a differential pair.

66. Apparatus according to claim 65, wherein each of said antenna assemblies includes at least one conductive strip disposed between the adjacent ones of said conductive strips of adjacent transmission channels, and said means for isolating said channels so as to minimize cross talk between said channels includes means for connecting each said at least one conductive strip to ground.

67. Apparatus according to claim 64, wherein said second antenna assembly includes, for each of said channels, at least four of said conductive strips spaced apart from one another and extending around the periphery of said drum, each of said strips terminating at its opposite ends at a predetermined location in its characteristic impedance.

68. Apparatus according to claim 57, wherein
said memos for transferring data includes a first transceiver assembly coupled to said first antenna assembly;
a second transceiver assembly coupled to said second antenna assembly; and means, coupled to each of said antenna assemblies, for generating an encoded data signal as a function of said data encoded in accordance with a predetermined protocol; and wherein each of said transceiver assemblies includes means for modulating said encoded data signal so as to produce a modulated encoded data signal for transmission across said gap, and means for demodulating said modulated encoded data signal so as to generate said encoded data signal, and means for decoding said encoded data signal in accordance with said protocol so as to produce said data signal.

69. Apparatus according to claim 68, wherein said means for modulating said encoded data signal includes means for modulating said encoded data signal in accordance with frequency shift keying said encoded data signal.

70. Apparatus according to claim 68, wherein said means for generating the encoded data signal, encodes the data in accordance with an ETHERNET protocol.

71. Apparatus according to claim 70, wherein ETHERNET protocol is the ISO/IEC8802-3 (ethernet) P.L. (10 Base 5) protocol.

72. An apparatus for simultaneously bidirectionally transferring data between a first device and a second device mounted for movement with respect to the first device, the apparatus comprising:

a first antenna assembly fixed relative to the first device;

a second antenna assembly fixed relative to and sufficiently disposed on said second device such that said first antenna assembly and said second antenna assembly are in communicating relationship substantially throughout the entire range of movement of said second device relative to said first device, and so that a spatial gap is provided between said first and second antenna assemblies as said second device moves with respect to said first device, wherein said first and second antenna assemblies are capacitively coupled to one another; and means for simultaneously bidirectionally transferring data from said first device to said second device and from said second device to said first device as said second device moves relative to said first device.

73. Apparatus according to claim 72, wherein said means for transferring data includes a first transceiver assembly coupled to said first antenna assembly, and a second transceiver assembly coupled to said second assembly.

74. Apparatus according to claim 73, wherein each of said transceiver assemblies is adapted to simultaneously transmit and receive data transmitted across said gap.

75. Apparatus according to claim 74, wherein said apparatus further including means for transmitting data from said first device to said second device through at least one data transmission channel, and means for transmitting data from said second device to said first device through at least one additional transmission channel, and means for isolating said data transmission channels so as to minimize cross talk between said data transmission channels.

* * * * *

UNITED STATES PATENT AND TRADEMARK OFFICE
CERTIFICATE OF CORRECTION

PATENT NO. : 5,577,026
DATED : November 19, 1996
INVENTOR(S) : Gordon et al.

It is certified that error appears in the above-indentified patent and that said Letters Patent is hereby corrected as shown below:

Claim 68, column 21, line 57, delete "memos" and substitute therefor -- means --.

Signed and Sealed this

Twenty-eighth Day of January, 1997

Attest:

BRUCE LEHMAN

*Attesting Officer*  *Commissioner of Patents and Trademarks*